United States Patent [19]

Harada et al.

[11] Patent Number: 5,195,999
[45] Date of Patent: Mar. 23, 1993

[54] ABSORBENT BODY AND ABSORBENT ARTICLE

[75] Inventors: Nobuyuki Harada, Suita; Kazumasa Kimura, Ikoma; Tadao Shimomura, Toyonaka, all of Japan

[73] Assignee: Nippon Shokubai Co., Ltd., Osaka, Japan

[21] Appl. No.: 751,988

[22] Filed: Aug. 29, 1991

[30] Foreign Application Priority Data

Aug. 30, 1990 [JP] Japan .................................. 2-226682
Aug. 30, 1990 [JP] Japan .................................. 2-226683

[51] Int. Cl.$^5$ ...................... A61F 13/15; B32B 13/20; D04H 1/58
[52] U.S. Cl. .................... 604/368; 604/358; 604/367; 428/284; 428/288; 428/913
[58] Field of Search .................. 604/358, 367, 368; 428/284, 288, 913

[56] References Cited

U.S. PATENT DOCUMENTS 4,424,247 1/1984 Erickson .............................. 428/284
5,079,034 1/1992 Miyake et al. ...................... 427/348

FOREIGN PATENT DOCUMENTS 0349241 1/1990 European Pat. Off. ............ 604/358

Primary Examiner—Randall L. Green
Assistant Examiner—Paul Zuttarelli
Attorney, Agent, or Firm—Burns, Doane, Swecker & Mathis

[57] ABSTRACT

An absorbent body having an absorbent polymer and hydrophilic fibers as main components thereof, characterized by the fact that the density of said absorbent body is in the range of from 0.1 to 0.5 g/cm$^3$ or a ratio of wet swelling is not less than 200%, a capacity of said absorbent body for absorption of physiological saline solution under pressure is in the range of from 11 to 25 g/g, and the ratio of exfoliation of said absorbent polymer is not more than 45%, and an absorbent article comprising a liquid-pervious surface material, a liquid-impervious lining material, and the absorbent body layer interposed therebetween.

16 Claims, 1 Drawing Sheet

ABSORBENT BODY AND ABSORBENT ARTICLE

BACKGROUND OF THE INVENTION

1. Field of the Invention

This invention relates to a novel thin absorbent body having an absorbent polymer and hydrophilic fibers as main components thereof and an absorbent article using the absorbent body.

2. Description of the Prior Art

Most of the absorbent bodies in such absorbent articles as disposable diapers and sanitary napkins which are currently in the market have been changing to composites of such hydrophilic fibers as fluffy pulp and paper with absorbent polymers. The requirements which an absorbent body using an absorbent polymer in a relatively large amount is expected to fulfil include capacity for absorption, small thickness and light weight, and shape-retaining property, for example. It is necessary that these functions should be wholly satisfied.

The absorbent bodies which are now in use are nearly satisfactory in terms of capacity for absorption but are not satisfactory in terms of small thickness and light weight and shape-retaining property. Thus, the manufacture of an absorbent article which has small thickness and light weight, possesses a large capacity for absorption, suffers from no serious leakage, and therefore fully satisfies producers and consumers alike has not been materialized to date.

An object of this invention, therefore, is to provide a novel absorbent body and an absorbent article.

Another object of this invention is to provide an absorbent body which has small thickness and light weight, possesses a large capacity for absorption, and suffers from no serious leakage and an absorbent article using the absorbent body.

SUMMARY OF THE INVENTION

The objects described above are accomplished by an absorbent body having an absorbent polymer and hydrophilic fibers as main components thereof, which absorbent body is characterized by having a density in the range of from 0.1 to 0.5 $g/cm^3$, an amount of absorption of physiological saline solution under pressure in the range of from 11 to 25 g/g, and a ratio of exfoliation of absorbent polymer of not more than 45%.

These objects are further accomplished by an absorbent article comprising a liquid-pervious surface material, a liquid-impervious lining material, and an absorbent layer interposed therebetween, which absorbent article is characterized by the fact that the absorbent body set forth in the preceding paragraph forms part or the whole of the absorbent layer.

The objects are also accomplished by an absorbent body having an absorbent polymer and hydrophilic fibers as main components thereof, which absorbent body is characterized by having an amount of absorption under pressure of physiological saline solution in the range of from 11 to 25 g/g, a ratio of exfoliation of absorbent polymer of not less than 45%, and a ratio of wet swelling of not less than 200%.

The objects are accomplished by an absorbent article comprising a liquid-pervious surface material, a water-impervious lining material, and an absorbent layer interposed therebetween, which absorbent article is characterized by the fact that the absorbent body set forth in the preceding paragraph forms part or the whole of the absorbent layer.

The inventors continued a diligent study on absorbent bodies with a view to developing an absorbent article having small thickness and light weight, possessing a large capacity for absorption, and suffering from no serious leakage. As a result, they have succeeded in perfecting this invention by the use of an absorbent body whose density, amount of absorption under pressure, and ratio of exfoliation of absorbent polymer are severally controlled in prescribed ranges.

Since the absorbent body obtained in the present invention has such a construction as described above, it serves as an ideal absorbent for various absorbent articles in the medical and sanitary fields such as sanitary napkins, disposable diapers, pads for children and adults suffering from incontinence, pads for excessively secreting breasts, and medical pads. It is also useful for various applications requiring to retain and absorb water such as, for example, freshness-retaining materials, agricultural-horticultural water-retaining materials, and industrial water-retaining materials.

EXPLANATION OF THE PREFERRED EMBODIMENT

Figure 1:
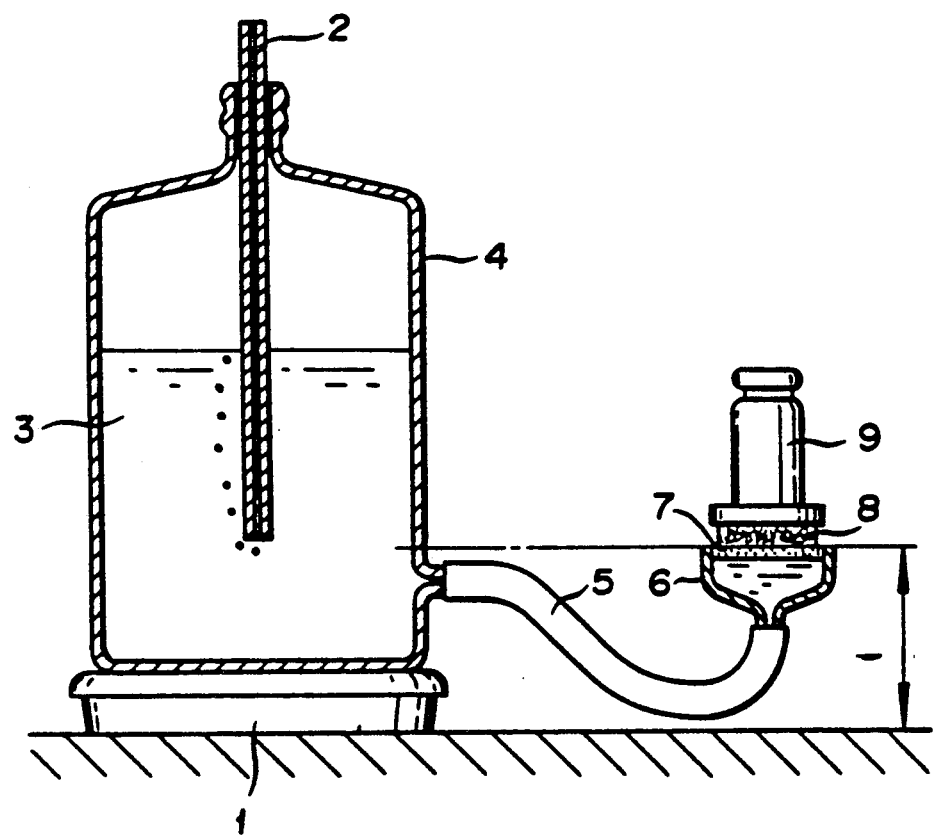
FIG. 1 is a schematic cross section illustrating an apparatus to be used in this invention for the determination of an amount of absorption under pressure.

For this invention, it is important that since the absorbent body is made mainly of an absorbent polymer, it should excel in ability to absorb liquid and possess satisfactorily small thickness and avoid exfoliation of the absorbent polymer after absorption of liquid. It is further important that the absorbent body should be capable of absorbing and diffusing liquid without inducing the phenomenon of gel blocking and incapable of inducing exfoliation of the absorbent polymer after absorption of liquid.

The absorbent body is not disintegrated even after absorbing liquid because it has a small ratio of exfoliation of absorbent polymer. Even when it is used in absorbing liquid for the second time or the third time, therefore, it is capable of quickly absorbing urine and menstruation without a sacrifice of its wicking speed. Thus, it warrants production of an absorbent article which suffers from no conspicuous leakage and enables the wearer to enjoy a sensation of dryness. Further, the amount of absorption under pressure of the absorbent body constitutes itself an important factor for the production of an absorbent article because an unduly small or large amount of absorption under pressure prevents the absorbent body from acquiring a desired reduction in weight, causes breakage in the absorbent body, and compels the absorbent body to suffer from leakage. If the density is unduly small, since the absorption and diffusion of liquid are retarded and the leakage of liquid is suffered to occur conspicuously, the absorbent body is not allowed a substantial reduction in thickness and consequently is prevented from finding practical utility. It is only by the use of an absorbent exhibiting density, amount of absorption under pressure, and ratio of exfoliation of absorbent polymer in balanced magnitudes that the production of an absorbent article enjoying freedom from objectionable feeling and possessing small thickness and light weight is rendered possible.

If the ratio of wet swelling is unduly small, since the absorption and diffusion of liquid are retarded and the leakage of liquid is suffered to occur conspicuously, the absorbent body is not allowed a substantial reduction in thickness and consequently is prevented from finding practical utility. It is, therefore, only by the use of an absorbent body exhibiting ratio of wet swelling, amount of absorption under pressure, and ratio of exfoliation in balanced magnitudes that the production of an absorbent article enjouing freedom from unpleasantness and possessing sufficiently small thickness and light weight is materialized.

For this invention, it is further important that the absorbent body mentioned above should be produced by mixing the mixture of an absorbent polymer with synthetic pulp (gravimetric ratio of 100:1-30) in the presence of water with hydrophilic fibers in a gravimetric ratio in the range of 100:5-500, preferably 100:10-200, based on the absorbent polymer and thermally compressing the resultant mixture to a density in the range of from 0.1 to 0.5 g/cm$^3$, preferably from 0.15-0.4 g/cm$^3$.

For the purpose of restraining the ratio of exfoliation of absorbent polymer, a method for solidifying the absorbent polymer by the use of a varying binder and a method for enclosing the absorbent polymer with a fibrous matrix have been proposed, for example. In the absorbent bodies which are produced by these methods, there generally exists the relation of contradiction between the ratio of exfoliation and the amount of absorption under pressure.

None of the currently commercially available absorbent bodies satisfies all of the aforementioned physical properties, i.e. the density in the range of from 0.1 to 0.5 g/cm$^3$, the amount of absorption of physiological saline solution under pressure in the range of from 11 to 25 g/g, and the ratio of defoliation of absorbent polymer of not more than 45%.

None of the currently commercially available absorbent bodies satisfies all of the aforementioned physical properties; i.e. the amount of absorption of physiological saline water under pressure in the range of from 11 to 25 g/g, the ratio of exfoliation of absorbed polymer of not more than 45%, and the ratio of wet swelling of not less than 200%.

To satisfy all of these physical properties, the absorbent body should be what is produced by mixing the mixture of an absorbent polymer with synthetic pulp (gravimetric ratio 100:1-30) in the presence of water with hydrophilic fibers in a gravimetric ratio in the range of 100:5-500, based on the absorbent polymer and thermally compressing the resultant mixture to a density in the range of from 0.1 to 0.5 g/cm$^3$.

The absorbent polymer for use in the present invention generally is only required to possess absorbency. The absorbent polymers which answer this description include, in addition to (cross-linked) polymers of water-soluble ethylenically unsaturated monomers having (meth)acrylic acids or salts thereof as main components and optionally incorporating a cross-linking agent therein, cross-linked derivatives of polyethylene oxide, polyvinyl pyrrolidone, sulfonated polystyrene, and polyvinyl pyridine, saponified starch-poly(meth)acrylonitrile graft polymers, starch-poly(meth)acrylic acid (and salts thereof) graft copolymers (and cross-linked derivatives thereof), starch-poly(meth)acrylic ester graft copolymers (and cross-linked derivatives thereof), and hydrolyzed starch-poly(meth)acrylic ester graft copolymers, for example. Among other absorbent polymers cited above, the (cross-linked) polymers of water-soluble ethylenically unsaturated monomers having acrylic acid or an acrylate as a main component prove to be preferable and cross-linked polymers of acrylic acid (salts thereof) to be more preferable. This invention does not discriminate the absorbent polymer on account of the method to be used for the production thereof. Optionally two or more of these absorbent polymers may be jointly used. The absorbent polymer to be used consists of substantially dry particles which are capable of absorbing physiological saline solution in a ratio exceeding 5 g/g, preferably falling in the range of from 20 to 80 g/g and more preferably in the range of from 35 to 60 g/g. The absorbent polymer by nature generally contains water to a certain extent. The expression "substantially dry" as used herein means the state in which the individual particles are incapable of mutually adhering in the normal atmosphere. The shapes which the particles are required to assume in order to ensure effective use herein include various forms of powder such as spheres, granules, randomly shaped particles, and foamed particles and fibrillar particles. These particles may be simple particles or pelletized particles. These particles are allowed to have a cross-link degree gradient near their surface regions. In the case of a powder, the agglomerates thereof are preferable to have diameters such that the weight average particle diameter is in the range of from 10 to 1,000 microns, preferably 100 to 700 microns.

The hydrophilic fibers which are effectively used in the present invention include wood pulp fibers such as mechanical pulp, chemical pulp, and dissolved pulp and manmade cellulosic fibers such as rayon and acetate, for example. In the present invention, the hydrophilic fibers may partly incorporate therein additionally such synthetic fibers as nylon, polyesters, and polyolefins. Preferable hydrophilic fibers are represented by wood pulp fibers. The amount of the hydrophilic fibers to be used herein is in the range of from 5 to 500 parts by weight, preferably from 10 to 200 parts by weight, based on 100 parts by weight of the absorbent polymer.

In the present invention, the hydrophilic fibers may be used jointly with synthetic pulp. The amount of the synthetic pulp to be used additionally is in the range of from 1 to 30 parts by weight, preferably from 2 to 25 parts by weight, based on 100 parts by weight of the absorbent polymer. The synthetic pulp to be used in the present invention is known in the art. For example, see "Pulp, Synthetic," Kirk-Othmer, Encyclopedia of Chemical Technology, 3rd Ed.(New York: 1982), Vol. 19, pp. 420-435 . The pulps are very fine, highly branched, discontinuous fibrils made from thermoplastic resins. Their visual appearance and dimensions closely resemble those of wood pulp. The thermoplastic resins which are effectively usable herein for the production of the synthetic pulp include polyolefins, polyesters, polyacrylonitrile, and other hydrophobic thermoplastic resins, for example. Among other thermoplastic resins cited above, polyolefins formed of one or more α-olefins such as polyethylene, polypropylene, ethylene-propylene copolymer, ethylene-1-butene copolymer, propylene-1-butene copolymer, and ethylene-4methyl-1-pentene copolymer prove to be particularly preferable because they are capable of notably improving the hydrophilicity of the hydrophilic fibers. Methods for the production of synthetic pulp from thermoplastic resin are disclosed in JP-B-47-21,898(1972), JP- B-47-32,133(1972), JP-A-3-180,504(1991), JP-A-3-180,505(1991), and JP-B-52-47,049(1977). The products of such methods are available under trademark designations such as, for example, SWP (Mitsui Petrochemical Industries, Ltd.) PULPLUS (E.I. du Pont de Nemours & Company), and PULPEX (Hercules Incorporated). The absorbent body of the present invention is produced by the following methods, for example.

(1) A method which produces an absorbent body having density in the range of from 0.1 to 0.5 g/cm$^3$ by mixing 100 parts by weight of an absorbent polymer with 1 to 30 parts by weight of synthetic pulp during addition thereto of 1 to 40 parts by weight of water, dry mixing the resultant mixture with 5 to 500 parts by weight of hydrophilic fibers such as ground pulp, based on 100 parts by weight of the absorbent polymer, molding the produced mixture in the form of web, and thermally compressing the web to the density mentioned above.

(2) A method which produces an absorbent body having density in the range of from 0.1 to 0.5 g/cm$^3$ by mixing 100 parts by weight of an absorbent polymer with 1 to 30 parts by weight of synthetic pulp wetted with 1 to 40 parts by weight of water, dry mixing the resultant mixture with 5 to 500 parts by weight of hydrophilic fibers such as ground pulp, based on 100 parts by weight of the absorbent polymer, molding the produced mixture in the form of web, and thermally compressing the web to the density mentioned above.

The absorbent body which is produced as described above possesses specific physical properties, i.e. density in the range of from 0.1 to 0.5 g/cm$^3$, preferably from 0.15 to 0.4 g/cm$^3$, amount of absorption of physiological saline solution under pressure in the range of from 11 to 25 g/g, preferably from 12 to 20 g/g, and ratio of exfoliation of absorbent polymer of not more than 45%, preferably not more than 30%.

The absorbent body which is produced as described above possesses physical properties such as amount of absorption of physiological saline solution under pressure in the range of from 11 to 25 g/g, preferably from 12 to 20 g/g, ratio of exfoliation of absorbent polymer of not more than 45%, preferably not more than 30%, and ratio of wet swelling of not less than 200%, preferably in the range of from 220 to 600%.

The absorbent body could be made to acquire an amount of absorption of even not less than 30 g/g by suitably varying the mixing ratio of the component materials. For the reason given above, the absorbent body having this large amount of absorption is deficient in stability to resist the influence of wetness and in efficiency of absorption and, therefore, is unpreferable. If the absorbent body has a ratio of exfoliation of absorbent polymer of not less than 45%, a disposable diaper, for example, which uses this absorbent body has the disadvantage that the diaper worn by an infant sustains leakage when the absorbent body used therein is fractured by the motion of the infant's body. If the absorbent body has an amount of absorption under pressure of less than 11 g/g, it has the disadvantage that the absorbent body is deficient in ability of absorption and, therefore, is not allowed a preferred reduction in thickness or weight. In view of the various factors described above, it may well be concluded that the most preferable absorption properties to be possessed by the absorbent body are density in the range of 0.1 to 0.5 g/cm$^3$, amount of absorption under pressure in the range of 11 to 25 g/g, and ratio of exfoliation of absorbent polymer of not more than 45%.

In view of the various factors described above, it may well be concluded that the most preferable above, it may well be concluded that the most preferable absorption properties to be possessed by the absorbent body are amount of absorption under pressure in the range of from 11 to 25 g/g, ratio of exfoliation of absorbent polymer of not more than 45%, and ratio of wet swelling of not less than 200%.

The application to an absorbent article of the absorbent body of this invention which satisfies all of the absorption properties may be effected by simply interposing the absorbent body of the present invention between a liquid-pervious sheet and a liquid-impervious sheet which are other indispensable component parts of the absorbent article or by jointly using the absorbent body of this invention and a known absorbent body such as of fluffy pulp as an absorbent layer.

The liquid-impervious sheets which are effectively usable in the present invention include sheetlike substances of such soft synthetic resins as polyethylene, polypropylene, vinyl chloride resin, nylon, and vinylon, for example. The liquid-pervious surface materials which are effectively usable herein include non-woven fabrics of natural fibers (such as, for example, wood or cottom fibers), synthetic fibers (such as, for example, polyester or polyolefin fibers), or combinations of natural fibers and synthetic fibers, perforated plastic films, porous foamed materials, and reticular foamed articles, for example.

The absorbent body and absorbent article as embodiments of the present invention have been described. It should be noted that this invention need not be limited to these embodiments but may be practiced otherwise without departing from the spirit of the invention.

Now, the present invention will be described below with reference to working examples. Wherever the term "parts" is mentioned in the following referential examples, working examples, and controls, it shall be construed as "parts by weight" unless otherwise specified.

Test for Quality

The absorbent bodies produced were evaluated by the following methods:

1. Amount of Absorption under Pressure

An apparatus which, as illustrated in FIG. 1, comprised a container 4 for an aqueous 0.9% physiological saline solution 3 mounted on a balance 1 and provided with an ambient air inlet pipe 2, an inverse funnel 6 communicating via a conduit 5 with the container 4, and a glass filter 7 attached to the top part of the inverse funnel 6 was used. The capacity of a given absorbent body 8 for absorption (g/g) was determined by mounting the absorbent body 8 on the filter 7, superposing a weight 9 on the absorbent body 8, allowing the absorbent body to stand under a load of 30 g/cm$^2$ for 30 minutes, and measuring the amount of the saline solution absorbed by the absorbent body during this standing. In this test, a circular sample 5.5 cm in diameter from the absorbent body 8 was used.

2. Density of Absorbent Body

The density of a given absorbent body was determined by placing a 10 cm square sample from the absorbent body under a load of 7 g/cm$^2$, measuring the height, z (mm), of the square sample in the pressed state, dividing the weight, x (g), of the sample by the volume, 10 z (cm$^3$), and reporting the quotient.

3. Ratio of Exfoliation of Absorbent Polymer

This property of a given absorbent body was determined by placing a 2 cm×4 cm rectangular sample from a given absorbent body into 100 cc of physiological saline solution kept stirred (at a rate of 100 rpm by the use of a stirrer) in a 11-cc beaker, keeping the sample in the stirred saline solution for 10 minutes, removing the sample from the saline solution, weighing the absorbent polymer fallen from the sample into the saline solution during the standing in the stirred saline solution, and calculating the ratio of exfoliation of the absorbent polymer in accordance with the following formula.

Ratio of exfoliation (%) = {(Amount of exfoliated polymer (g))/ (Amount of polymer in original sample (g))} × 100

REFERENTIAL EXAMPLE 1

In an atmosphere of nitrogen, 4,000 parts of an aqueous solution of 37% an acrylic monomer composed of 74.98 mol% of sodium acrylate, 25 mol% of acrylic acid, and 0.02 mol%, of trimethylolpropane triacrylate was polymerized by being stirred with 2.0 parts of sodium persulfate and 0.08 part of l-ascorbic acid, to produce a gel hydrated polymer finely divided in a particle diameter of about 5 mm. The gel hydrated polymer was dried with a hot air drier at 150 ° C., pulverized with a hammer type pulverizing device, and sifted with a 20-mesh metallic gauze to separate a 20-mesh pass powder (having an average particle diameter of 405 microns). Then, 100 parts of the separated powder was mixed with 0.5 part of glycerol, 2 parts of water, and 2 parts of ethyl alcohol and the resultant mixture was heat-treated at 210° C., to produce an absorbent polymer A having the surface region thereof secondarily cross-linked. The capacity of this polymer for absorption of physiological saline solution was found to be 50 g/g.

REFERENTIAL EXAMPLE 2

In an atmosphere of nitrogen, 4,000 parts of an aqueous solution of 37% acrylic monomer composed of 74.95 mol% of sodium acrylate, 25 mol% of acrylic acid, and 0.05 mol% of trimethylolpropane triacrylate was polymerized by being stirred with 2.0 parts of sodium persulfate and 0.08 part of l-ascorbic acid, to produce a gel hydrated polymer finely divided in a particle diameter of about 5 mm. The gel hydrated polymer was dried with hot air drier at 150° C., pulverized with a hammer type pulverizing device, and sifted with a 20-mesh metallic gauze to separate a 20-mesh pass powder as an absorbent polymer B (having an average particle diameter of 350 microns). The capacity of this absorbent polymer for absorption of physiological saline solution was found to be 46 g/g.

REFERENTIAL EXAMPLE 3

By mixing 100 parts of the absorbent polymer B produced in Referential Example 2 with 0.5 part of glycerol, 2 parts of water, and 2 parts of ethyl alcohol and then heat-treating the resultant mixture at 210° C., an absorbent polymer C having the surface region thereof secondarily cross liked was obtained. The capacity of this absorbent polymer for absorption of physiological saline solution was found to be 43 g/g.

REFERENTIAL EXAMPLE 4

An absorbent polymer D (having particle diameters of 250 to 149 microns) was separated by classifying the absorbent polymer C produced in Referential Example 3 with 60- to 100-mesh sieves. The capacity of the absorbent polymer D for absorption of physiological saline solution was found to be 42 g/g.

EXAMPLE 1

One hundred (100) parts by weight of the absorbent polymer A and 25 parts by weight of synthetic pulp (produced by Mitsui Petrochemical Industries, Ltd. and marketed under product code of "SWP UL-415") were mixed while the addition of 25 parts by weight of water thereto was continued. In a mixer, the resultant mixture was dry mixed with 125 parts by weight of ground pulp. The produced mixture was pneumatically molded in the form of sheet on a wire screen with the aid of a batch type pneumatic molding device, to produce a web measuring 14 cm×40 cm in area and having a basis weight of 0.047 g/cm$^2$. The produced web was compressed and heated at 150° C. for 10 minutes, to produce an absorbent body (1) of this invention having a density of 0.16 g/cm$^3$. The capacity of the absorbent body (1) for absorption under pressure was found to be 16.5 g/g, the ratio of exfoliation of absorbent polymer to be 19%, and the ratio of wet swelling to be 256%.

EXAMPLE 2

An absorbent body (2) of this invention having a basis weight of 0.051 g/cm$^2$ and a density of 0.13 g/cm$^3$ was produced by following the procedure of Example 1, except that the amount of water was changed to 32 parts by weight, that of the synthetic pulp to 17 parts by weight, and that of the ground pulp to 133 parts by weight. The capacity of the absorbent body (2) for absorption under pressure was found to be 16.0 g/g, the ratio of exfoliation of absorbent polymer to be 22%, and the ratio of wet swelling to be 210%.

EXAMPLE 3

One hundred (100) parts by weight of the absorbent polymer A was mixed with 7 parts by weight of synthetic pulp wetted in advance with 5 parts by weight of water. In a mixer, the resultant mixture was dry mixed with 67 parts by weight of ground pulp. The produced mixture was pneumatically molded on a wire screen with the aid of a batch type pneumatic molding device, to produce a web measuring 14 cm×40 cm in area and having a basis weight of 0.042 g/cm$^2$. The web was compressed and heated at 150° C. for 10 minutes, to produce an absorbent body (3) of this invention having a density of 0.02 g/cm$^3$. The capacity of the absorbent body (3) for absorption under pressure was found to be 15.8 g/g, the ratio of exfoliation of absorbent polymer to be 20%, and the ratio of wet swelling to be 270%.

EXAMPLE 4

One hundred (100) parts by weight of the absorbent polymer C was mixed with 13 parts by weight of synthetic pulp (produced by Mitsui Petrochemical Industries, Ltd. and marketed under product code of "SWP UL-415") while the addition of 20 parts by weight of water thereto was continued. In a mixer, the resultant mixture was dry mixed with 100 parts by weight of ground pulp. The produced mixture was pneumatically molded on a wire screen with the aid of a batch type pneumatic molding device, to produce a web measuring 14 cm×40 cm in area. The web was interposed between two opposed tissue papers having a basis weight of 0.0013 g/cm$^2$ and then emboss pressed at 150° C. for one minute, to produce an absorbent body (4) of this invention having a basis weight of 0.054 g/cm$^2$ and a density of 0.27 g/cm$^3$. The capacity of the absorbent body (4) for absorption was found to be 14.4 g/g, the ratio of exfoliation of absorbent polymer to be 6%, and the ratio of wet swelling to be 300%.

EXAMPLE 5

An absorbent body (5) of this invention having a basis weight of 0.044 g/cm$^2$ and a density of 0.22 g/cm$^3$ was obtained by following the procedure of Example 4, except that the amount of the ground pulp was changed to 66 parts by weight. The capacity of this absorbent body (5) for absorption under pressure was found to be 17.3 g/g, the ratio of exfoliation of absorbent polymer to be 7%, and the ratio of wet swelling to be 325%.

EXAMPLE 6

An absorbent body (6) of this invention having a basis weight of 0.029 g/cm$^2$ and a density of 0.30 g/cm$^3$ was obtained by following the procedure of Example 4, except that the amount of the synthetic pulp was changed to 15 parts by weight and that of the ground pulp to 34 parts by weight. The capacity of the produced absorbent body (6) for absorption under pressure was found to be 16.3 g/g, the ratio of exfoliation of absorbent polymer to be 19%, and the ratio of wet swelling to be 300%.

EXAMPLE 7

One hundred (100) parts by weight of the absorbent polymer C was mixed with 12 parts by weight of synthetic pulp (produced by Mitsui Petrochemical Industries, Ltd. and marketed under product code of "SWP UL-415") during continued addition of 20 parts by weight of water thereto. Then, in a mixer, the resultant mixture was dry mixed with 131 parts by weight of ground pulp. The produced mixture was pneumatically molded on a wire screen with the aid of a batch type pneumatic molding device, to produce a web measuring 14 cm×40 cm in area. The web was interposed between two opposed tissue papers having a basis weight of 0.0013 g/cm$^2$ and then emboss pressed at 150° C. for one minute, to produce and absorbent body (7) of this invention having a basis weight of 0.047 g/cm$^2$ and a density of 0.24 g/cm$^3$. The capacity of the absorbent body (7) for absorption under pressure was found to be 12.5 g/g, the ratio of exfoliation of absorbent polymer to be 8%, and the ratio of wet swelling to be 275%.

EXAMPLE 8

An absorbent body (8) of this invention having a basis weight of 0.050 g/cm$^2$ and a density of 0.25 g/cm$^3$ was produced by following the procedure of Example 7, except that the amount of the synthetic pulp was changed to 5 parts by weight and that of the ground pulp to 100 parts by weight. The capacity of the absorbent body (8) for absorption under pressure was found to be 15.3 g/g, the ratio of exfoliation of absorbent polymer to be 13%, and the ratio of wet swelling to be 225%.

EXAMPLE 9

An absorbent body (9) of this invention having a basis weight of 0.060 g/cm$^2$ and a density of 0.30 g/cm$^3$ was produced by following the procedure of Example 7, except that the amount of the synthetic pulp was changed to 23 parts by weight and that of the ground pulp to 133 parts by weight. The capacity of the absorbent body (9) for absorption under pressure was found to be 13.5 g/g, the ratio of exfoliation of absorbent polymer to be 12%, and the ratio of wet swelling to e 400%.

EXAMPLE 10

An absorbent body (10) of this invention having a basis weight of 0.070 g/cm$^2$ and a density of 0.35 g/cm$^3$ was produced by following the procedure of Example 7, except that the amount of the synthetic pulp was changed to 24 parts by weight and that of the ground pulp to 167 parts by weight. The capacity of the absorbent body (10) for absorption under pressure was found to be 12.3 g/g, the ratio of exfoliation of absorbent polymer to be 15%, and the ratio of wet swelling to be 400%.

EXAMPLE 11

An absorbent body (11) of this invention having a basis weight of 0.044 g/cm$^2$ and a density of 0.33 g/cm$^3$ was produced by following the procedure of Example 9, except that the amount of the ground pulp was changed to 67 parts by weight. The capacity of the absorbent body (11) for absorption under pressure was found to be 14.2 g/g and the ratio of defoliation of absorbent polymer to be 10%, and the ratio of wet swelling to be 333%.

EXAMPLE 12

One hundred (100) parts by weight of the absorbent polymer D was mixed with 13 parts by weight of synthetic pulp (produced by Mitsui Petrochemical Industries, Ltd. and marketed under product code of "SWP UL-415") during continued addition of 20 parts by weight of an aqueous 30 wt % aluminum polychloride solution thereto. Then, in a mixer, the resultant mixture was dry mixed with 100 parts by weight of ground pulp. The produced mixture was pneumatically molded on a wire screen with the aid of a batch type pneumatic molding device, to produce a web measuring 14 cm×40 cm in area. The produced web was interposed between two opposed tissue papers having a basis weight of 0.0013 g/cm$^2$ and then emboss pressed at 150° C. for one minute, to produce an absorbent body (12) of this invention having a basis weight of 0.042 g/cm$^2$ and a density of 0.21 g/cm$^3$. The capacity of the absorbent body (12) for absorption under pressure was found to be 13.2 g/g, the ratio of exfoliation of absorbent polymer to be 5%, and the ratio of wet swelling to be 350%.

EXAMPLE 13

One hundred (100) parts by weight of the absorbent polymer B and 13 parts by weight of synthetic pulp (produced by Mitsui Petrochemical Industries, Ltd. and marketed under product code of "SWP UL-415") were mixed while the addition of 20 parts by weight of 1% by weight aqueous solution of ethyleneglycol diglycidyl ether (product of Nagase Kasei K.K. and marketed under Denacol EX-810) thereto was continued. In a mixer, the resultant mixture was dry mixed with 67 parts by weight of ground pulp. The produced mixture was pneumatically molded in the form of sheet on a wire screen with the aid of a batch type pneumatic molding device, to produce a web measuring 14 cm×40 cm in area. The web was interposed between two opposed tissue papers having a basis weight of 0.0013 g/cm² and then emboss pressed at 150° C. for 1 minute, to produce an absorbent body (13) of this invention having a basis weight of 0.047 g/cm² and a density of 0.23 g/cm³. The capacity of the absorbent body (13) for absorption under pressure was found to be 13.7 g/g, the ratio of exfoliation of absorbent polymer to be 3%, and the ratio of wet swelling to be 250%.

EXAMPLE 14

An absorbent body (14) of this invention having a basis weight of 0.043 g/cm² and a density of 0.22 g/cm³ was produced by following the procedure of Example 8, except that the amount of synthetic pulp was changed to 7 parts by weight. The capacity of the absorbent body (14) for absorption under pressure was found to be 15.3 g/g, the ratio of exfoliation of absorbent polymer to be 14%, and the ratio of wet swelling to be 300%.

EXAMPLE 15

One hundred (100) parts by weight of the absorbent polymer C and 13 parts by weight of synthetic pulp (produced by Mitsui Petrochemical Industries Ltd. and marketed under product code of "SWP UL-415") were mixed while the addition of 20 parts by weight of water thereto was continued. In a mixer, the resultant mixture was dry mixed with 100 parts by weight of ground pulp. The produced mixture was pneumatically molded in the form of sheet on a wire screen with the aid of a batch type pneumatic molding device, to produce a web measuring 14 cm×40 cm in area. The web was interposed between two opposed tissue papers having a basis weight of 0.002 g/cm² and then emboss pressed at 200° C. for 10 seconds, to produce an absorbent body (15) of this invention having a basis weight of 0.052 g/cm² and a density of 0.26 g/cm³. The capacity of the absorbent body (15) for absorption under pressure was found to be 14.5 g/g, the ratio of exfoliation of absorbent polymer to be 11%, and the ratio of wet swelling to be 300%.

EXAMPLE 16

One hundred (100) parts by weight of the absorbent polymer C and 10 parts by weight of synthetic pulp (produced by Mitsui Petrochemical Industries, Ltd. and marketed under product code of "SWP UL-415") were mixed while the addition of 20 parts by weight of water thereto was continued. In a mixer, the resultant mixture was dry mixed with 133 parts by weight of ground pulp. The produced mixture was pneumatically molded in the form of sheet on a wire screen with the aid of a batch type pneumatic molding device, to produce a web measuring 14 cm×40 cm in area. The web was interposed between two opposed tissue papers having a basis weight of 0.002 g/cm² and then emboss pressed at 150° C. for 10 minutes, to produce an absorbent body (16) of this invention having a basis weight of 0.092 g/cm² and a density of 0.23 g/cm³. The capacity of the absorbent body (16) for absorption under pressure was found to be 13.5 g/g, the ratio of exfoliation of absorbent polymer to be 29%, and the ratio of wet swelling to be 350%.

EXAMPLE 17

One hundred (100) parts by weight of the absorbent polymer A was mixed with 8 parts by weight of synthetic pulp, while the addition of 20 parts by weight of water thereto was continued. In a mixer, the resultant mixture was dry mixed with 70 parts by weight of ground pulp. The produced mixture was pneumatically molded on a wire screen with the aid of a batch type pneumatic molding device, to produce a web. On one hand, another web comprising 35 parts by weight of ground pulp and 0.7 parts by weight of synthetic pulp were prepared, and a web measuring 14 cm×40 cm in area and having a basis weight of 0.046 g/cm² was prepared by interposing the former web with these two latter webs. The web was compressed and heated at 150° C. for 1 minute, to produce an absorbent body (17) of this invention having a density of 0.23 g/cm³. The capacity of the absorbent body (17) for absorption under pressure was found to be 13.5 g/g, the ratio of exfoliation of absorbent polymer to be 20%, and the ratio of wet swelling to be 352%.

EXAMPLE 18

One hundred (100) parts by weight of the absorbent polymer D was mixed with 20 parts by weight of synthetic pulp while the addition of 20 parts by weight of water thereto was continued. In a mixer, the resultant mixture was dry mixed with 18 parts by weight of ground pulp. The produced mixture was pneumatically molded on a wire screen with the aid of a pneumatic molding device, to produce a web. The web was interposed between two opposed tissue papers having a basis weight of 0.0013 g/cm² and then emboss pressed at 150° C. for 1 minute, to produce an absorbent body (18) of this invention having a basis weight of 0.019 g/cm² and a density of 0.25 g/cm³. The capacity of the absorbent body (18) for absorption was found to be 18.0 g/g, the ratio of exfoliation of absorbent polymer to be 35%, and the ratio of wet swelling to be 375%.

EXAMPLE 19

One hundred (100) parts by weight of the absorbent polymer A and 13 parts by weight of synthetic pulp (produced by Mitsui Petrochemical Industries, Ltd. and marketed under product code of "SWP UL-415") were mixed while the addition of 10 parts by weight of water thereto was continued. The produced mixture was interposed between two webs comprising 33 parts by weight of ground pulp to produce a web measuring 14 cm×40 cm in area and having a basis weight of 0.052 g/cm². The produced web was emboss compressed and heated at 150° C. for 1 minute, to produce an absorbent body (19) of this invention having a density of 0.17 g/cm³. The capacity of the absorbent body (19) for absorption under pressure was found to be 12.5 g/g, the ratio of exfoliation of absorbent polymer to be 33%, and the ratio of wet swelling to be 233%.

EXAMPLE 20

One hundred (100) parts by weight of the absorbent polymer C and 20 parts by weight of synthetic pulp (produced by Mitsui Petrochemical Industries, Ltd. and marketed under product code of "SWP UL-415") were mixed while the addition of 20 parts by weight of water thereto was continued. In a mixer, the resultant mixture was dry mixed with 60 parts by weight of ground pulp. The produced mixture was pneumatically molded in the form of sheet on a wire screen with the aid of a batch type pneumatic molding device, to produce a web measuring 14 cm×40 cm in area. A web comprising 30 parts by weight group pulp was put on one surface of the produced web, and the web thus obtained was interposed between two opposed tissue papers having a basis weight of 0.0013 g/cm$^2$ and then passed between hot rollers to heat at 200° C. for 20 seconds and to obtain an absorbent body (20) of this invention having a basis weight of 0.048 g/cm$^2$ and a density of 0.16 g/cm$^3$. The capacity of the absorbent body (20) for absorption under pressure was found to be 12.2 g/g, the ratio of exfoliation of absorbent polymer to be 14%, and the ratio of wet swelling to be 210%.

Control 1

One hundred (100) parts by weight of the absorbent polymer C was mixed with 33 parts by weight of synthetic pulp (produced by Mitsui Petrochemical Industries, Ltd. and marketed under product code of "SWP UL-415") during continued addition of 20 parts by weight of water thereto. Then, in a mixer, the resultant mixture was dry mixed with 100 parts by weight of ground pulp. The produced mixture was pneumatically molded on a wire screen with the aid of a batch type pneumatic molding device, to produce a web measuring 14 cm×40 cm in area. The web was interposed between two opposed tissue papers having a basis weight of 0.0013 g/cm$^2$ and then emboss pressed at 150° C. for one minute to produce an absorbent body (1) for comparison having a basis weight of 0.048 g/cm$^2$ and a density of 0.24 g/cm$^3$. The capacity of the absorbent body (1) for comparison was found to be 10.2 g/g, the ratio of exfoliation of absorbent polymer to be 17%, and the ratio of wet swelling to be 250%.

Control 2

One hundred (100) parts by weight of the absorbent polymer C was mixed with 66 parts by weight of synthetic pulp (produced by Mitsui Petrochemical Industries, Ltd. and marketed under product code of "SWP UL-415") during continued addition of 20 parts by weight of water thereto. Then, in a mixer, the resultant mixture was dry mixed with 100 parts by weight of ground pulp. The produced mixture was pneumatically molded on a wire screen with the aid of a batch type pneumatic molding device, to produce a web measuring 14 cm×40 cm in area. The produced web was interposed between two opposed tissue papers having a basis weight of 0.0013 g/cm$^2$ and then emboss pressed at 150° C. for one minute, to produce an absorbent body (2) for comparison having a basis weight of 0.056 g/cm$^2$ and a density of 0.28 g/cm$^3$. The capacity of the absorbent body (2) for comparison for absorption under pressure was found to be 8.8 g/g, the ratio of exfoliation of absorbent polymer to be 5%, and the ratio of wet swelling to be 275%.

Control 3

In a mixer, 100 parts by weight of the absorbent polymer C was dry mixed with 100 parts by weight of ground pulp. Then, the resultant mixture was pneumatically molded on a wire screen with the aid of a batch type pneumatic molding device, to produce a web measuring 14 cm×40 cm in area. The web was interposed between two opposed tissue papers having a basis weight of 0.0013 g/cm$^2$ and then emboss pressed at 150° C. for one minute, to produce an absorbent body (3) for comparison having a basis weight of 0.043 g/cm$^2$ and a density of 0.17 g/cm$^3$. The capacity of the absorbent body (3) for comparison for absorption under pressure was found to be 12.3 g/g, the ratio of exfoliation of absorbent polymer to be 76%, and the ratio of wet swelling to be 240%.

Control 4

In a mixer, 100 parts by weight of the absorbent polymer C was dry mixed with 13 parts by weight of synthetic pulp (produced by Mitsui Petrochemical Industries, Ltd. and marketed under product code of "SWP UL-415") and 100 parts by weight of ground pulp. The resultant mixture was pneumatically molded on a wire screen with the aid of a batch type pneumatic molding device, to produce a web measuring 14 cm×40 cm in area. The web was interposed between two opposed tissue papers having a basis weight of 0.0013 g/cm$^2$ and then emboss pressed at 150° C. for one minute, to produce an absorbent body (4) for comparison having a basis weight of 0.049 g/cm$^2$ and a density of 0.25 g/cm$^3$. The capacity of the absorbent body (4) for comparison for absorption under pressure was found to be 10.9 g/g, the ratio of exfoliation of absorbent polymer to be 53%, and the ratio of wet swelling to be 250%.

Control 5

One hundred (100) parts by weight of the absorbent polymer C was mixed with 13 parts by weight of synthetic pulp (produced by Mitsui Petrochemical Industries, Ltd. and marketed under product code of "SWP UL-415") during continued addition of 20 parts by weight of water thereto. Then, in a mixer, the resultant mixture was dry mixed with 100 parts by weight of ground pulp. The produced mixture was pneumatically molded on a wire screen with the aid of a batch type pneumatic molding device, to produce a web measuring 14 cm×40 cm in area. The web was interposed between two opposed tissue papers having a basis weight of 13 g/m$^2$ and then heated at 150° C. for 10 minutes, to produce an absorbent body (5) for comparison having a basis weight of 0.050 g/cm$^2$ and a density of 0.08 g/cm$^3$. The capacity of the absorbent body (5) for comparison for absorption under pressure was found to be 13.9 g/g, the ratio of exfoliation of absorbent polymer to be 56%, and the ratio of wet swelling to be 100%.

EXAMPLE 21

A disposable diaper comprising a liquid-pervious polypropylene top sheet, two tissue papers, a 9 cm×35 cm rectangular sample of the absorbent body (1) of this invention (weighing 15 g), a liquid-impervious polyethylene back sheet containing leg gathers, and two tape fasteners was manually assembled by tying the component parts with a double-face adhesive tape. The total weight of the diaper was 33 g.

The diaper was tried on a one-year old infant (having 10 kg of body weight) in comparison with a diaper (having a total weight of 50 g) currently available in the market. The diaper using the absorbent body of this invention was found to excel preeminently in shape-retaining property after absorption of urine and suffered only sparingly from leakage.

EXAMPLE 22

Disposable diapers using absorbent bodies of varying properties were manufactured by following the procedure of Example 21. These diapers were tested for one month by a panel of seven mothers. Each panelist randomly received 30 diapers and tried them on her child. After the test, the diapers were tested for ratio of test diaper leaked and shape-retaining property of absorbent body. The results are shown in Table 1. It is clearly noted from the table that the absorbent articles using the absorbent bodies of this invention possessed outstanding absorption characteristics.

TABLE 1

| Absorbent body No | Density (g/cm³) | Amount of absorption under pressure (g/g) | Ratio of exfoliation of absorbent polymer (%) | Ratio of test diaper leaked (%) | Shape-retaining property of absorbent body |
| --- | --- | --- | --- | --- | --- |
| A | 0.27 | 14.4 | 6 | 3 | good |
| B | 0.24 | 12.5 | 8 | 10 | good |
| C | 0.25 | 15.3 | 13 | 7 | good |
| D | 0.26 | 14.5 | 11 | 7 | good |
| E | 0.29 | 8.8 | 5 | 33 | good |
| F | 0.25 | 10.9 | 53 | 27 | decomposition |
| G | 0.08 | 13.9 | 56 | 17 | decomposition |

What is claimed is:

1. An absorbent body having absorbent polymer particles and hydrophilic fibers as main components thereof, wherein said absorbent polymer is a cross-linked polymer of a water-soluble ethylenic monomer having acrylic acid or an acrylate as a main component; said absorbent body having a density in a range of from 0.1 to 0.5 g/cm³, a capacity for absorption of physiological saline solution under a load in a range of from 11 to 25 g/g, and a ratio of exfoliation of not more than 45%.

2. An absorbent body according to claim 1, wherein said hydrophilic fibers are present in an amount within a range of from 5 to 500 parts by weight, based on 100 parts by weight of said absorbent polymer.

3. An absorbent body according to claim 2, which further comprises 1 to 30 parts by weight of synthetic pulp, based on 100 parts by weight of said absorbent polymer.

4. An absorbent body having absorbent polymer particles and hydrophilic fibers as main components thereof, wherein said absorbent polymer is a cross-linked polymer of a water-soluble ethylenic monomer having acrylic acid or an acrylate as a main component thereof; said absorbent body having a capacity for absorption of physiological saline solution under a load in a range of 11 to 25 g/g, a ratio of exfoliation of said absorbent polymer of not more than 45%, and a ratio of wet swelling of not less than 200%.

5. An absorbent body according to claim 4, wherein said hydrophilic fibers are present in an amount within a range of from 5 to 500 parts by weight, based on 100 parts by weight of said absorbent polymer.

6. An absorbent body according to claim 5, which further comprises 1 to 30 parts by weight of synthetic pulp, based on 100 parts by weight of said absorbent polymer.

7. An absorbent article comprising a liquid-pervious surface material, a liquid-impervious lining material, and an absorbent layer interposed therebetween, characterized by the fact that said absorbent layer at least partly comprises of an absorbent body having absorbent polymer particles and hydrophilic fibers as main components thereof, wherein said absorbent polymer is a cross-linked polymer of a water-soluble ethylenic monomer having acrylic acid or an acrylate as a main component thereof and said absorbent body exhibits density in a range of from 0.1 to 0.5 g/cm³, capacity for absorption of physiological saline solution under a load in a range of from 11 to 25 g/g, and a ratio of exfoliation of said absorbent polymer of not more than 45%.

8. An absorbent article according to claim 7, wherein said hydrophilic fibers are present in an amount within a range of from 5 to 500 parts by weight, based on 100 parts by weight of said absorbent polymer.

9. An absorbent article according to claim 8, wherein said absorbent body further comprises 1 to 30 parts by weight of synthetic pulp, based on 100 parts by weight of said absorbent polymer.

10. An absorbent article comprising a liquid-pervious surface material, a liquid-impervious lining material, and an absorbent layer interposed therebetween, characterized by the fact that said absorbent layer at least partly comprises of an absorbent body having absorbent polymer particles and hydrophilic fibers as main components thereof, wherein said absorbent polymer is a cross-linked polymer of a water-soluble ethylenic monomer having acrylic acid or an acrylate as a main component thereof, said absorbent body exhibits a capacity for absorption of physiological saline solution under a load in a range of from 11 to 25 g/g, a ratio of exfoliation of said absorbent polymer of not more than 45%, and a ratio of wet swelling of not less than 200%.

11. An absorbent article according to claim 10, wherein said hydrophilic fibers are present in an amount within a range of from 5 to 500 parts by weight, based on 100 parts by weight of said absorbent polymer.

12. An absorbent article according to claim 11, wherein said absorbent body further comprises 1 to 30 parts by weight of synthetic pulp, based on 100 parts by weight of said absorbent polymer.

13. An absorbent body having absorbent polymer particles and hydrophilic fibers as main components thereof, wherein said absorbent body has a density in the range of from 0.1 to 0.5 g/cm³, a capacity for absorption of physiological saline solution under a load in a range of 11 to 25 g/g, and a ratio of exfoliation of not more than 45%.

14. An absorbent body having absorbent polymer particles and hydrophilic fibers as main components thereof, wherein said absorbent body has a capacity for absorption of physiological saline solution under a load in the range of 11 to 25 g/g, a ratio of exfoliation of not more than 45%, and a ratio of wet swelling not less than 200%.

15. An absorbent article comprising a liquid-pervious surface material, a liquid-impervious lining material, and an absorbent layer interposed therebetween, characterized in that said absorbent layer at least partly comprises of an absorbent body having absorbent polymer particles and hydrophilic fibers as main components thereof, wherein said absorbent body has density in a range of from 0.1 to 0.5 g/cm³, a capacity for absorption of physiological saline solution under a load in a range of from 11 to 25 g/g, and ratio of exfoliation of not more than 45%.

16. An absorbent article comprising a liquid-pervious surface material, a liquid-impervious lining material, and an absorbent layer interposed therebetween, characterized in that said absorbent layer at least partly comprises an absorbent body having absorbent polymer particles and hydrophilic fibers as main components thereof, wherein said absorbent body has a capacity for absorption of physiological saline solution under a load in the range of from 11 to 25 g/g, a ratio of exfoliation of not more than 45%, and a ratio of wet swelling of not less than 200%.

* * * * *